United States Patent [19]

Smith

[11] Patent Number: Plant 6,101

[45] Date of Patent: Feb. 9, 1988

[54] EXEL'S EVERBEARING BLACKBERRY PLANT

[76] Inventor: Exel R. Smith, Box 229, Green Forest, Ark. 72638

[21] Appl. No.: 899,045

[22] Filed: Aug. 15, 1986

[51] Int. Cl.[4] ..... A01H 5/03

[52] U.S. Cl. ..... Plt./46

[58] Field of Search ..... Plt./46

*Primary Examiner*—Robert E. Bagwill

[57] ABSTRACT

An everbearing blackberry plant having undeveloped seeds.

6 Drawing Figures

1

This invention relates to a new and distinct hybrid blackberry plant that I have named Exel's Everbearing Blackberry. The plant was originated by my taking pollen from a flower of a Treeform blackberry and placing it on the stigmas of a flower of a Thornfree blackberry.

Out of this cross I selected the one plant that was outstanding and different in many ways from either parent plant or from any other blackberry plant I have seen.

Some of the differences are listed below:

I. Vigorous growth:
- A. *Breadth and height of one plant cluster.*—(Shown in FIG. 1).
- B. *Enormous size of stalk.*—(Shown in FIG. 2).

II. Reproduction:
- A. *New plants from tips of vines.*—New vines grow up almost erect in midsummer until they get above the height of the old vines. At that time they begin arching toward the ground. As they come in contact with the ground, they develop roots and form new plants.
- B. *New plants from roots.*—Less frequently than those from vine tips, new plants will shoot up from roots of the old plant at various distances away.
- C. *Vine-layering.*—I have also produced new plants by this method.
- D. *Conclusion.*—The parent plant and all other blackberry plants that I know reproduce in one way naturally, but this new plant reproducing naturally in the two ways stated in A and B makes it truly a new kind of blackberry.

2

III. Size of berries (Shown in FIG. 3):
- A. *Length.*—Generally over an inch.
- B. *Breadth.*—Approximately one inch.

IV. Taste:
- A. Good and sweet instead of the extremely sour taste of the Thornfree parent plant.
- B. Free of the bitter taste that most blackberries have.

V. Soft seeds: The seeds are soft since most of them are undeveloped, making the berries more palatable.

VI. Ripening: Berries begin ripening the latter part of June and continue to ripen in abundance until the middle of September when production begins tapering off; however, they continue to have ripe berries until the middle of October, making this new berry without any doubt an everbearing one. Thus, it is different from the parent plants or any other blackberry I know.

Proof can be seen in FIG. 4 showing the different stages of development from blossoms to ripe berries at the same time.

VII. Other characteristics:
- A. A slight lavender color of the flowers (FIG. 5).
- B. The almost bronze colored stem as the plant matures (FIG. 6).
- C. Purple color of leaves in late fall.
- D. Retention of some of the purple leaves all winter.

I claim:

1. A new and distinct hybrid everbearing blackberry which I have herein shown and described.

* * * * *

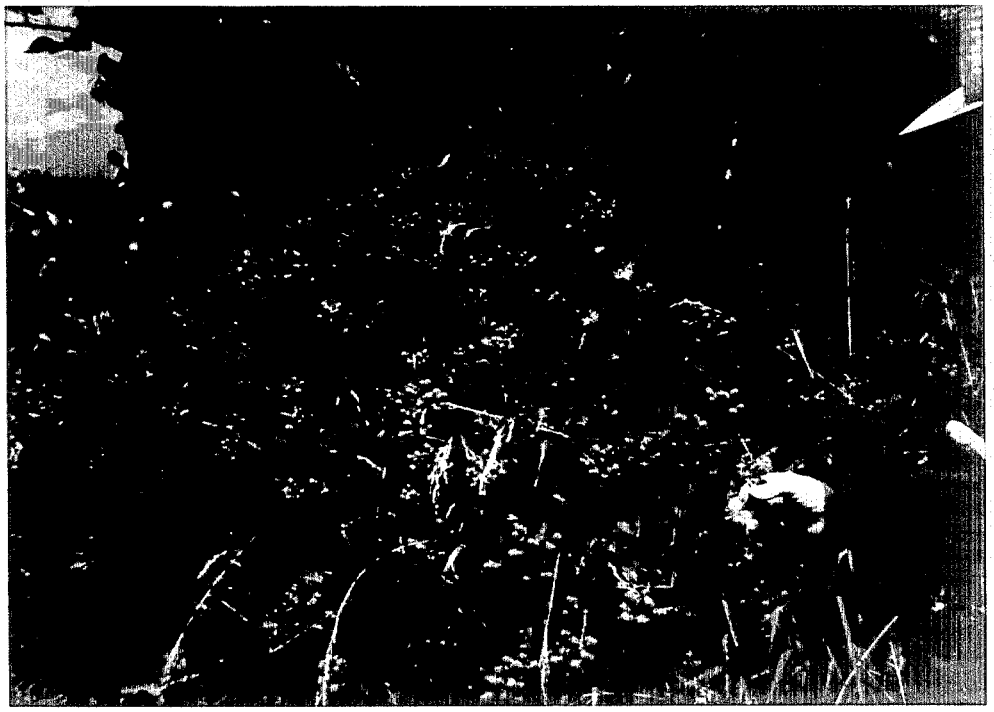
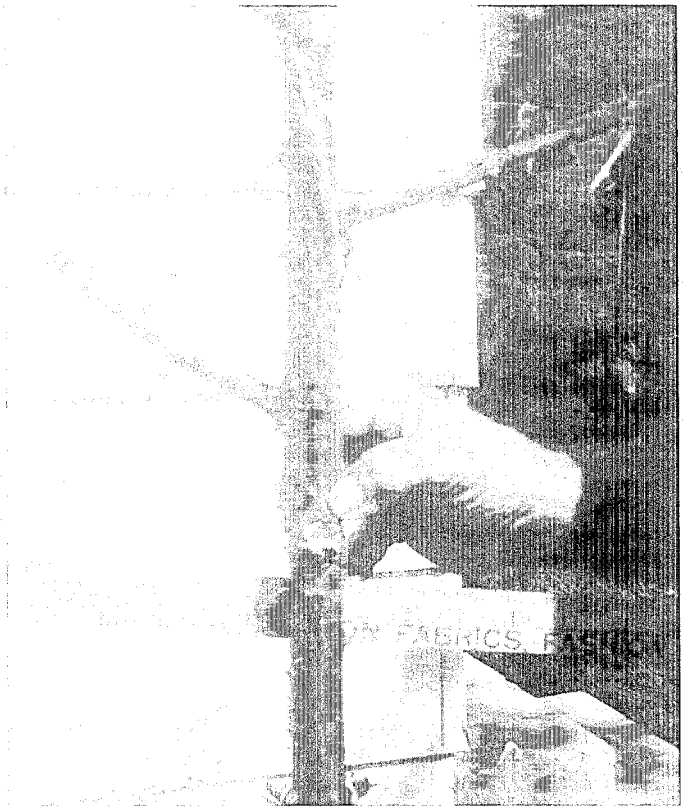

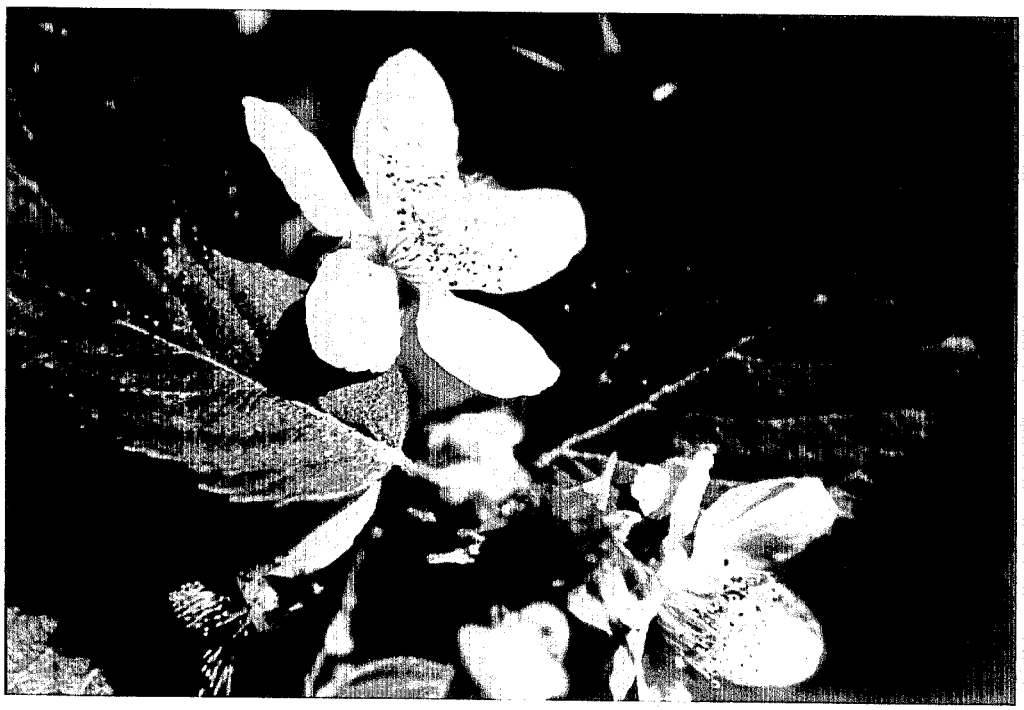
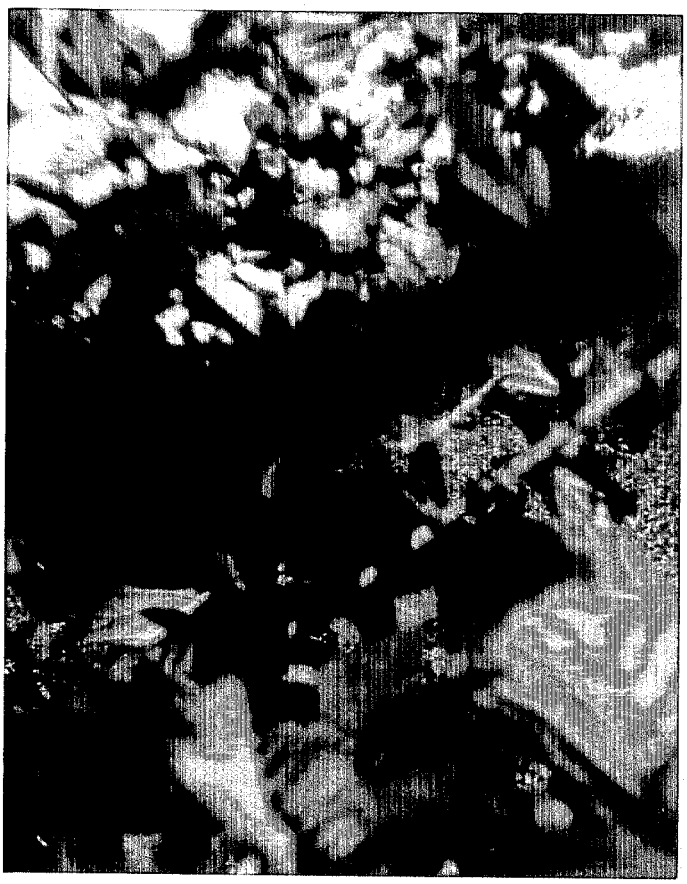

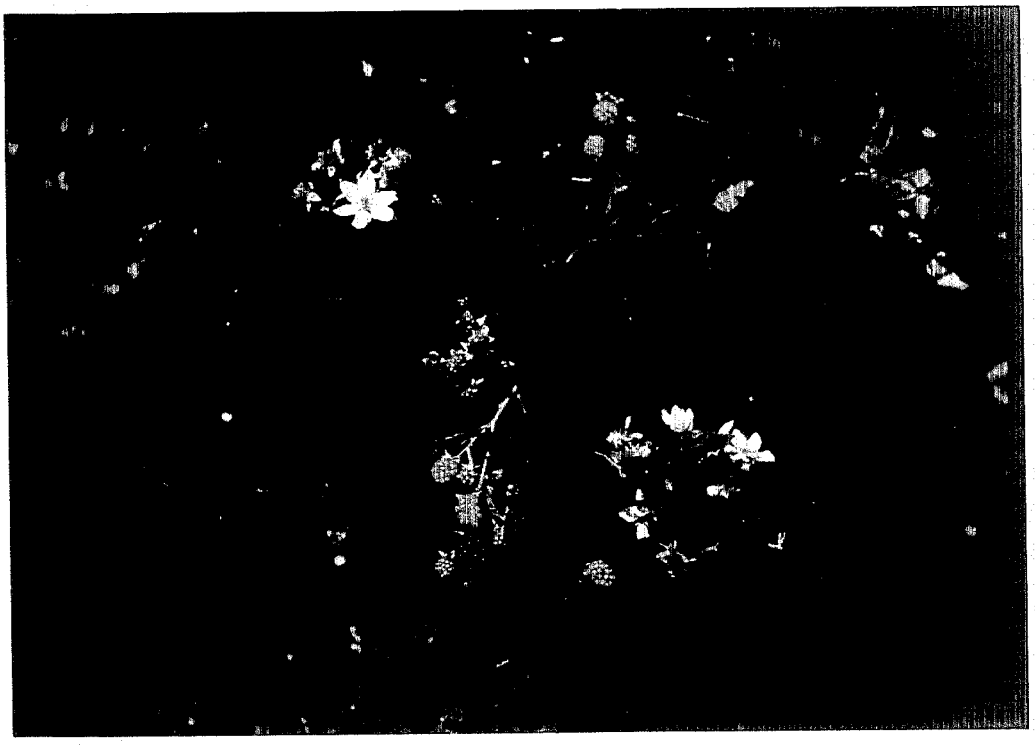

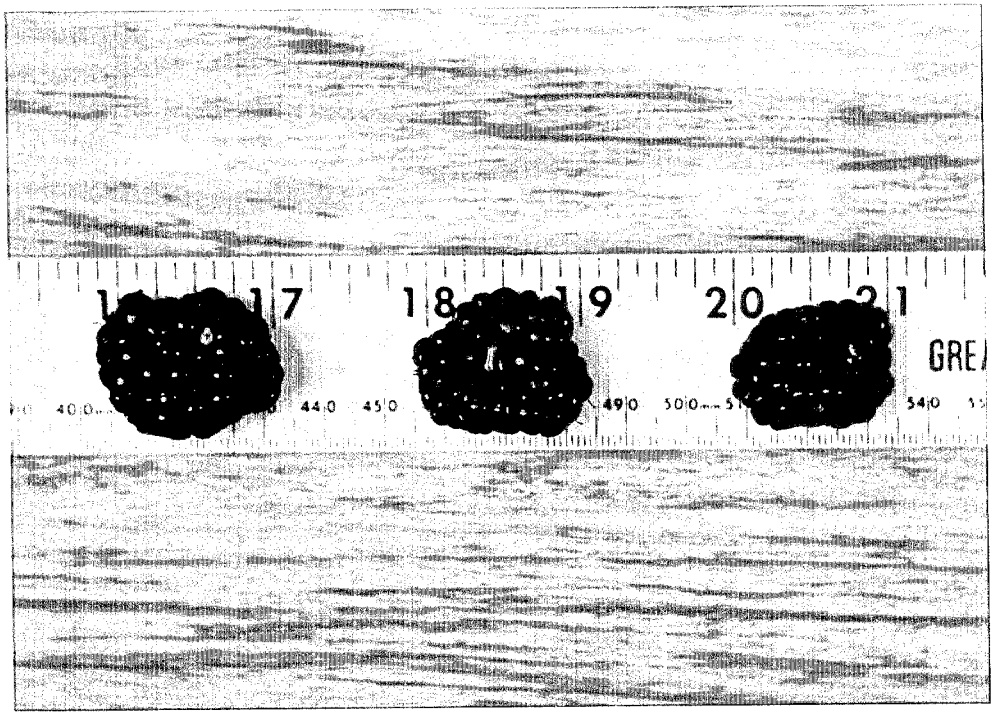
17
18
19
20
21
GRE
44.0
45.0
49.0
54.0